(12) United States Patent
Housley et al.

(10) Patent No.: US 6,949,673 B2
(45) Date of Patent: *Sep. 27, 2005

(54) PROCESS FOR PRODUCING CARBOXYLIC ACIDS

(75) Inventors: Samuel Duncan Housley, Yarm (GB); John A Turner, Stokesley (GB)

(73) Assignee: E.I. Du Pont de Nemours and Company, Wilmngton, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 10/393,971

(22) Filed: Mar. 21, 2003

(65) Prior Publication Data

US 2003/0229247 A1 Dec. 11, 2003

Related U.S. Application Data

(63) Continuation-in-part of application No. 09/884,381, filed on Jun. 19, 2001, now abandoned, which is a continuation-in-part of application No. 09/481,811, filed on Jan. 12, 2000, now abandoned, which is a continuation-in-part of application No. 09/757,458, filed on Jan. 9, 2001, now abandoned.

(51) Int. Cl.[7] .................. C07C 51/16; C07C 51/255
(52) U.S. Cl. .................. 562/412; 562/414; 562/413; 562/416; 562/77
(58) Field of Search .................. 562/414, 413, 562/77, 412, 416

(56) References Cited

U.S. PATENT DOCUMENTS

| 3,686,293 A | 8/1972 | Gualdi et al. |
| 4,269,805 A | 5/1981 | Schoengen et al. |
| 4,593,122 A | 6/1986 | Hashizume et al. |
| 5,004,830 A | 4/1991 | Park et al. |

FOREIGN PATENT DOCUMENTS

| WO | WO 98/38150 | * 9/1998 |
| WO | WO 99/31038 | 6/1999 |
| WO | WO 99/59953 | 11/1999 |

* cited by examiner

*Primary Examiner*—Cecilia J. Tsang
*Assistant Examiner*—Taylor Victor Oh
(74) *Attorney, Agent, or Firm*—Charles E. Krukiel

(57) ABSTRACT

Improved process for producing aromatic carboxylic acids by catalytic liquid phase oxidation of a corresponding precursor in a suitable solvent comprising feeding the reactants to a first oxidation reaction zone at high pressure and high solvent ratio, wherein uptake of oxygen is less than that required for full conversion of the precursor to its corresponding carboxylic acid, and then feeding the resulting reaction medium to a second oxidation reaction zone.

5 Claims, 3 Drawing Sheets

PROCESS FOR PRODUCING CARBOXYLIC ACIDS

CROSS REFERENCE TO RELATED APPLICATION

This application claims the benefit of U.S. application Ser. No. 09/481,811 filed Jan. 12, 2000, U.S. application Ser. No. 09/757,458 filed Jan. 9, 2001, both abandoned, and U.S. application Ser. No. 09/884,381 filed Jun. 19, 2001 now abandoned.

BACKGROUND OF THE INVENTION

The present invention relates to an improved process for producing aromatic carboxylic acids by catalytic liquid phase oxidation of a corresponding precursor in a suitable solvent. More particularly, the present invention is an improved process for catalytic liquid phase air oxidation of paraxylene to produce terephthalic acid which comprises sequential steps of feeding the reactants to a first reaction zone at elevated pressure wherein the temperature and the uptake of oxygen are controlled and any terephthalic acid which forms remains in solution, and then feeding the resulting reaction medium to a second reaction zone to complete the oxidation reaction.

Practically all terephthalic acid is produced on a commercial scale by catalytic, liquid phase air oxidation of paraxylene. Commercial processes use acetic acid as a solvent and a multivalent heavy metal or metals as catalyst. Cobalt and manganese are the most widely used heavy metal catalysts, and bromine is used as a renewable source of free radicals in the process.

Acetic acid solvent, air (molecular oxygen), paraxylene and catalyst are fed continuously into an oxidation reactor that is maintained at from 150° C. to 225° C. and from about 500 to 2,500 kPa (i.e., 5–25 atm). The feed solvent:paraxylene mass ratio is typically less than 5:1. Air is added in amounts in excess of the stoichiometric requirements for full conversion of the paraxylene to terephthalic acid, to minimize formation of undesirable by-products, such as color formers. The oxidation reaction is exothermic, and heat is removed by allowing the acetic acid solvent to vaporize. The corresponding vapor is condensed and most of the condensate is refluxed to the reactor, with some condensate being withdrawn to control reactor water concentration (two moles of water are formed per mole of paraxylene reacted). The residence time is typically 30 minutes to 2 hours, depending on the process. Depending on oxidation reactor operating conditions, e.g., temperature, catalyst concentration and residence time, significant degradation of the solvent and precursor can occur, which, in turn, can increase the cost of operating the process.

The effluent, i.e., reaction product, from the oxidation reactor is a slurry of crude terephthalic acid (TA) crystals which are recovered from the slurry by filtration, washed, dried and conveyed to storage. They are thereafter fed to a separate purification step or directly to a polymerization process. The main impurity in the crude TA is 4 carboxybenzaldehyde (4-CBA), which is incompletely oxidized paraxylene, although p-tolualdehyde and p-toluic acid can also be present along with undesirable color formers. By conducting the oxidation reaction according to the invention as described in greater detail below, it is possible to substantially reduce the formation of impurities in the final TA product and effectively control solvent and precursor degradation.

SUMMARY OF THE INVENTION

The present invention is an improved process for producing aromatic carboxylic acids by catalytic liquid phase oxidation of a corresponding precursor in a suitable solvent. In particular, the present invention is an improved process for the catalytic liquid phase oxidation of paraxylene to produce terephthalic acid. The process of the present invention comprises sequential steps of feeding the reactants, including a suitable solvent, to a first reaction zone at elevated pressure wherein the temperature and the uptake of oxygen are controlled and any terephthalic acid which forms remains in solution, and then feeding the resulting reaction medium to a second oxidation reaction zone.

In a preferred embodiment of the invention, the process comprises:

(a) feeding a solvent, an oxidation catalyst, paraxylene and a supply of oxygen to a first reaction zone to form a reaction medium in which the solvent:paraxylene mass ratio is in the range of from 5–30:1 and the operating pressure is in the range of at least about 2,500 kPa;

(b) limiting the uptake of oxygen within the reaction medium in the first reaction zone to a value which is less than that required for full conversion of the paraxylene to terephthalic acid such that any terephthalic acid which forms substantially remains in solution; and (c) feeding the reaction medium to a second reaction zone while simultaneously reducing the pressure of the reaction medium to a value in the range of from about 500 kPa to less than 2,500 kPa.

The resulting terephthalic acid can be recovered from the reaction medium exiting the second reaction zone by any convenient means.

While the preferred embodiment of the invention is described herein in terms of an improved oxidation system for converting paraxylene to terephthalic acid, it will be recognized that the invention is applicable to producing a range of aromatic carboxylic acids, and particularly phthalic acids, by catalytic liquid phase oxidation of a corresponding precursor in a suitable solvent. The invention resides in the discovery that the conversion of the precursor to its corresponding carboxylic acid can be substantially improved by carrying out the oxidation reaction in at least two stages, or zones, which comprise:

(1) feeding a solvent, an oxidation catalyst, a precursor, and a supply of oxygen to a relatively high pressure, e.g., at least about 2,500 kPa, first reaction zone to form a reaction medium in which the solvent:precursor mass ratio is in the range of from 5–30:1, preferably 10–20:1; and (2) feeding the reaction medium from the first reaction zone to a second reaction zone, where the oxidation reaction runs to completion, that is, substantially complete conversion of the precursor to the corresponding carboxylic acid.

In addition to maintaining the solvent:precursor mass ratio as described, the uptake of oxygen in the first reaction zone is limited to a value which is less than that required for full conversion of the precursor to its corresponding carboxylic acid. The corresponding carboxylic acid can have one or more acid groups, depending on the precursor.

Oxygen uptake in the first reaction zone is controlled by one or more of the following methods: (i) maintaining oxygen supply within a predetermined range; (ii) maintaining catalyst concentration within a predetermined range; (iii) limiting the residence time (defined as the reactor liquid volume divided by the reactor feed rate) within the first reaction zone to less than about 6 minutes, but preferably less than 4 minutes; and (iv) optionally removing heat from the reaction zone.

One aspect of the invention is limiting the uptake of oxygen within the reaction medium in the first reaction zone to a value less than that required for full conversion of the precursor to the corresponding aromatic carboxylic acid. Preferably, the oxygen uptake within the reaction medium in the first reaction zone is less than 70 percent of the oxygen required for full conversion of the precursor to the corresponding carboxylic acid.

Simultaneously while feeding the reaction medium to the second reactor the pressure of the reaction medium is reduced to a value in the range of from 500 kPa to less than 2,500 kPa. The carboxylic acid which results can be recovered from the final reaction medium, which is typically a slurry of acid crystals, by conventional methods.

In one embodiment of the invention, a feed stream comprising a solvent and an oxidation catalyst is prepared and oxygen is dissolved directly into the feed stream. The oxygenated feed stream is then fed continuously and simultaneously with the precursor into the first oxidation reaction zone, which is a plug flow reaction zone. Immediately upon entering the first reaction zone the precursor, e.g., paraxylene, is thoroughly mixed with the oxygenated solvent to initiate the reaction. By controlling the oxygen supply, catalyst concentration, residence time in and/or temperature of the first reaction zone, it is possible to control, i.e., limit, the uptake of oxygen within the reaction medium to a value which is less than that required for full conversion of the precursor to its corresponding carboxylic acid. The reaction medium is then fed to a second, more conventional, reactor as described above.

The process of the invention is particularly applicable to producing terephthalic acid by catalytic liquid phase oxidation of paraxylene in a solvent comprising acetic acid and water.

DETAILED DESCRIPTION OF THE INVENTION

Figure 1:
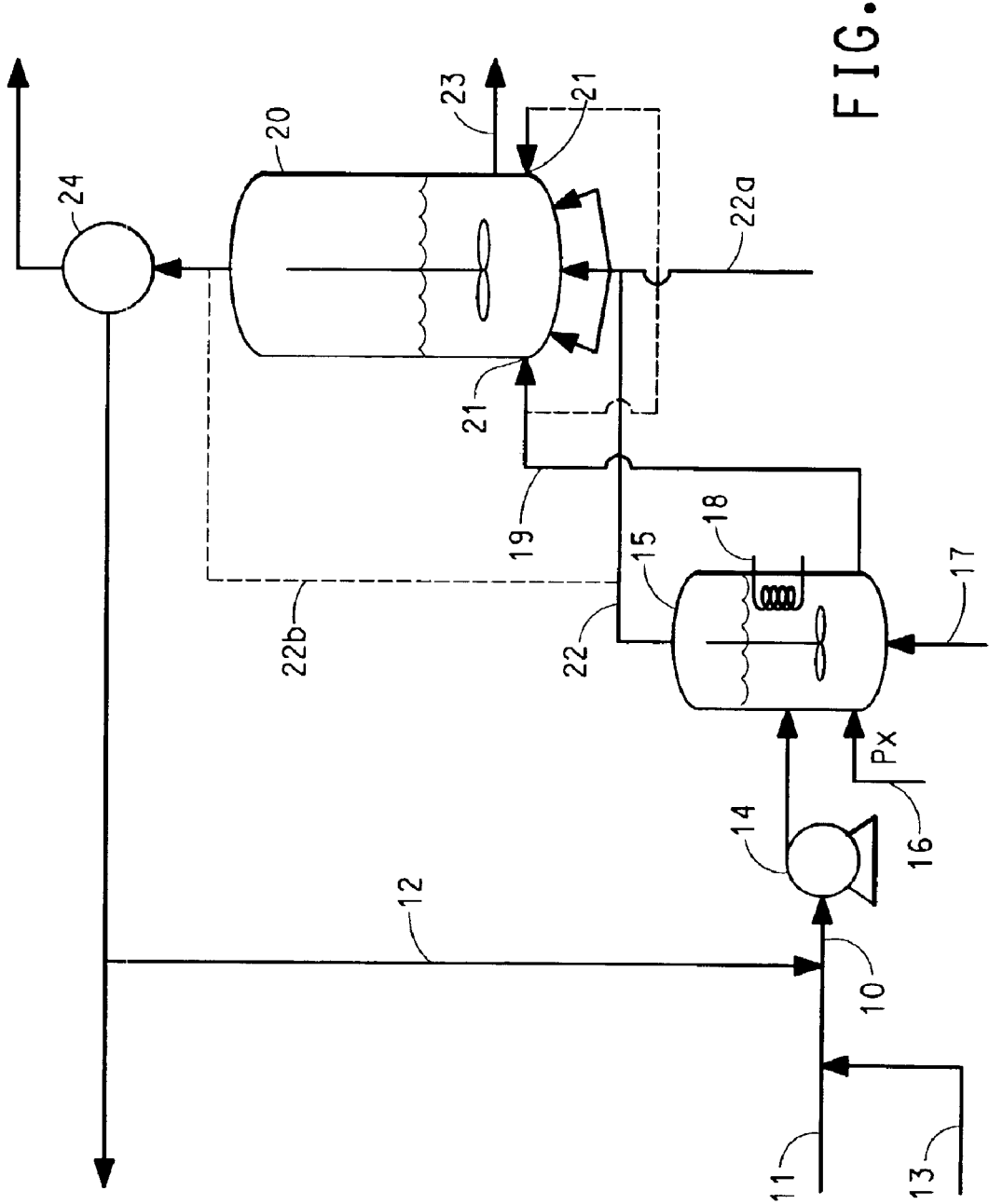
FIG. 1 is a simplified schematic diagram of the process of the invention according to one embodiment.

The present invention resides in the discovery that it is possible to produce aromatic carboxylic acids with improved efficiency and quality compared to the processes of the prior art. The present invention is characterized by a two-stage process. The first stage is carried out in a first reaction zone at a relatively high pressure, e.g., at least 2,500 kPa. The second stage is carried out in a second reaction zone at a lower pressure than the first stage, e.g., from about 500 to less than 2,500 kPa.

The first reaction zone of the process is characterized by a relatively high solvent:precursor mass ratio in the range of from 5–30:1, and a relatively high pressure, e.g., in the range of from at least 2,500 kPa up to 30,000 kPa or even higher. Best results for the overall process have been observed when the solvent:precursor mass ratio in the first reaction zone is in the range of from 10–20:1. For the purposes of this disclosure, the solvent:precursor mass ratio is defined as follows:

(a) the solvent mass flow is the total solvent flow through the first reaction zone, including any solvent recycled from the second reaction zone and downstream vessels, but excluding solvent recycled within the first reaction zone (b) the precursor mass flow is the total precursor flow to the process, whether the precursor is exclusively fed to the first reaction zone or whether a proportion is arranged to bypass the first reaction zone to be fed directly to the second reaction zone.

The first reaction zone is optionally cooled to control the temperature of the reaction medium as it exits the first reaction zone. Control of temperature, catalyst concentration, reactor residence time, and/or maintaining the oxygen supply to the first reaction zone within a predetermined range makes it possible to conveniently limit the uptake of oxygen within the reaction medium to a value which is less than that required for full conversion of the paraxylene to terephthalic acid.

Temperature control can be established, for example, by placing an internal cooling coil or other cooling device within the first reaction zone, by employing a cooling jacket to surround the reactor or by circulating the reaction medium through a heat exchanger located externally from the reactor.

Catalyst control can be established by, for example, routing some of the catalyst-containing mother liquor directly to the second reaction zone, bypassing the first reaction zone.

The invention is characterized in that the terephthalic acid (TA) formed in the first reaction zone remains substantially in solution. By "substantially," the inventors mean that it is preferred to have very little, e.g., less than about 10 percent by weight of solid TA precipitate from solution in the first reaction zone. It is more preferred to have only a trace, e.g., less than 1 percent of solid TA precipitate from solution in the first reaction zone. It is most preferred to avoid precipitation of solid terephthalic acid in the first reaction zone.

Formation of terephthalic acid in the first reaction zone is limited by limiting oxygen uptake in the first reaction zone. Precipitation of terephthalic acid is prevented by maintaining a high solvent:precursor mass ratio, by maintaining a sufficiently high reaction medium temperature, and by selecting an appropriate coolant (e.g., boiling water) and cooling means that avoids cold spots from forming at any location within the reaction zone.

On exiting the first reaction zone, the pressure of the reaction medium is reduced simultaneously as it is fed to a more conventional oxidation reactor. This reactor could typically be a stirred tank reactor or a bubble column reactor, for example. Pressure reduction can be conveniently accomplished by passing the reaction medium through one or a plurality of pressure letdown valves positioned about the periphery of the reactor. Best results have been obtained when the reaction medium is dispersed rapidly upon entering the second reactor. Rapid dispersion can be achieved by using established methods for dispersing paraxylene-containing feeds in conventional reactors. In a stirred tank reactor, for example, this would include injecting the reaction medium into the reactor below the liquid line in close proximity to the discharge from an agitator impeller. Rapid dispersion of the reaction medium can be achieved in a bubble column reactor by injecting the reaction medium in close proximity to the air feeds.

Referring now to the drawings, FIG. 1 is a simplified schematic diagram of the process of the invention according to one embodiment. As mentioned above, the process will be described as it relates to the production of terephthalic acid, although the invention is applicable to the production of a range of aromatic carboxylic acids and mixtures thereof.

In the illustrated embodiment shown in FIG. 1, the process is carried out by first forming a feed stream 10 comprising solvent, i.e., acetic acid and water, and oxidation catalyst. In practice the feed stream will comprise a mixture comprising (i) recycled solvent, recycled mother liquor and catalyst, line 11, (ii) reactor condensate from the second reactor, line 12, and (iii) fresh acetic acid make-up, line 13. The mixed feed stream will contain typical catalyst components (e.g., Co, Mn, Br), at generally diluted concentrations from what would normally be present when using a single conventional oxidation reactor. Optionally, but not shown, control of catalyst concentration in the first reaction zone can be achieved by bypassing some of the catalyst-containing mother liquor, line 11, directly to second reactor 20.

The mixed feed stream will generally have a temperature in the range of from 130° C. to 160° C., based on the temperature of the various components which form the feed stream. However, the temperature of the feed stream is not critical.

The pressure of feed stream 10 is raised via a suitable pump 14 to a value of at least about, but generally in excess of about, 2,500 kPa, and the feed stream is introduced continuously and simultaneously into a first stirred tank reactor 15 with paraxylene, via line 16, and a source of oxygen, via line 17.

The supply of oxygen via line 17 can be air, oxygen-enriched air, oxygen mixed with a gas such as, for example, carbon dioxide, or essentially pure oxygen. When the source of oxygen includes nitrogen or another sparingly soluble carrier gas, the extent of cooling in the first reaction zone and its operating pressure are preferably chosen such that the vapor present in the first reaction zone is fuel-lean, i.e., the hydrocarbon content of the vapor is below the Lower Explosive Limit (LEL). When the source of oxygen includes a soluble carrier gas or when essentially pure oxygen is used, the extent of cooling in the first reaction zone and its operating pressure are preferably chosen such that there is no vapor phase present in the first reaction zone. Optionally, but not shown in FIG. 1, some or all of the oxygen can be pre-dissolved directly into feed 10 via a mixing device located downstream of the feed pump 14.

The paraxylene feed 16 may optionally be pre-mixed with acetic acid solvent and introduced into the system either upstream or downstream of feed pump 14. Optionally, but not shown, a portion of paraxylene feed 16 may bypass reactor 15 and be fed directly to second reactor 20. The reaction medium which results in the first reactor, without us bypassing any paraxylene to the second reaction zone, has a solvent:paraxylene mass ratio in the range of from 5–30:1. Best results have been observed for this embodiment when the solvent:paraxylene mass ratio is in the range of from 10–20:1.

Figure 2:
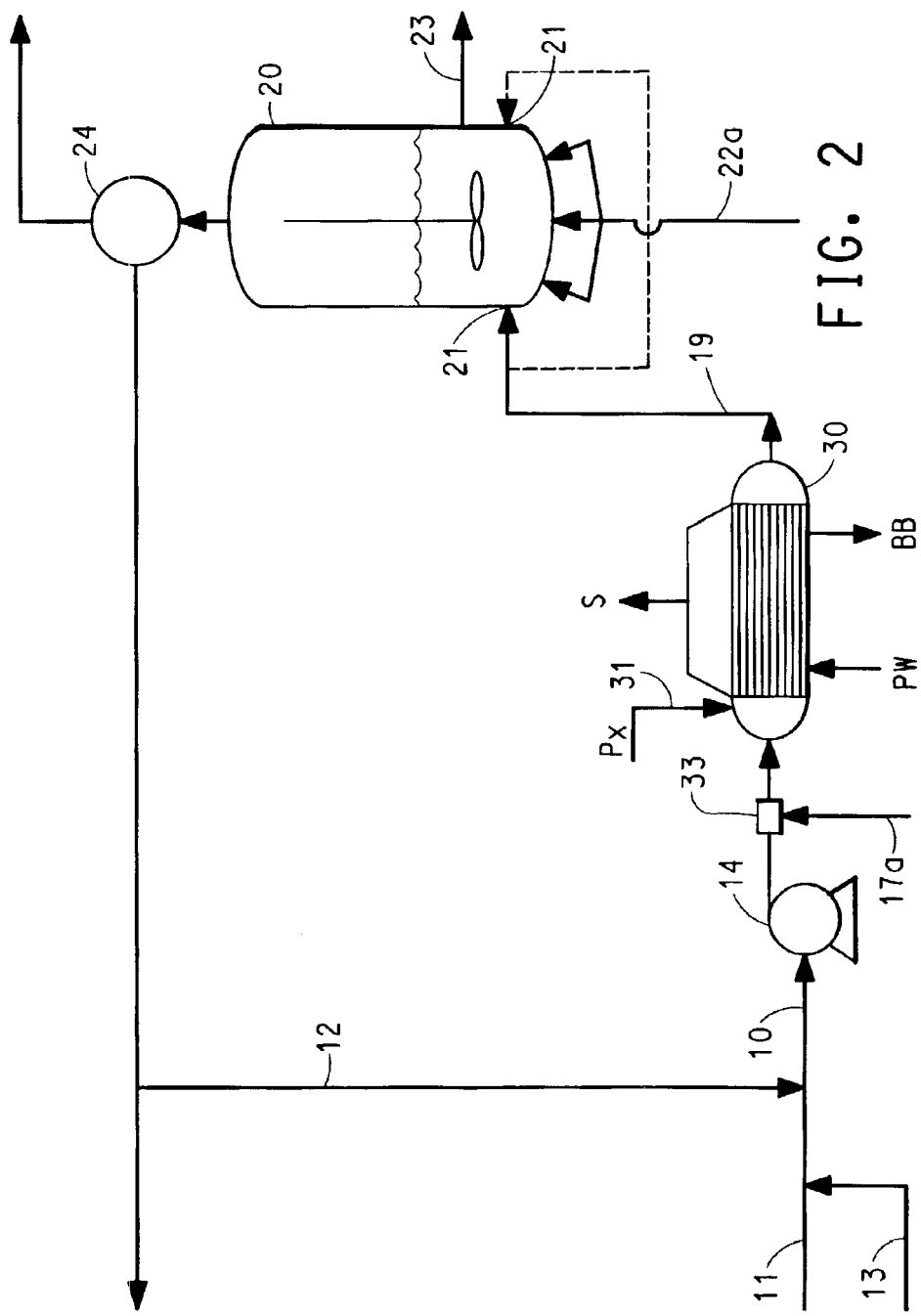
FIG. 2 is a simplified schematic diagram of the process of the invention according to a preferred embodiment.
Figure 3:
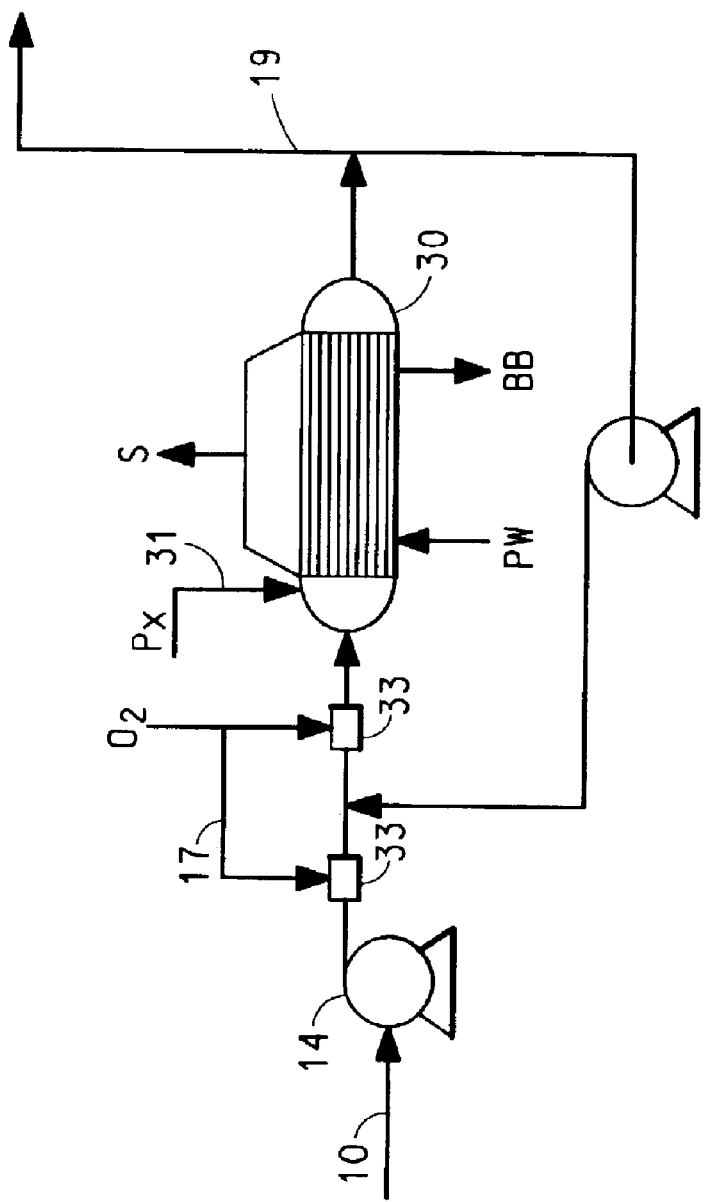
FIG. 3 is a simplified schematic diagram of an alternative to the process diagram shown in FIG. 2 wherein a pumped reactor recycle is illustrated.

In cases where a portion of the paraxylene feed, i.e., line 16 in FIG. 1 and line 31 in FIGS. 2 and 3, is arranged to bypass the first reactor and is fed directly to second reactor 20, the effective solvent:paraxylene mass ratio in the reaction medium in the first reactor will adjust upward in response to that portion of the paraxylene which bypasses the first reactor, and the resulting mass ratio may reach a value in the range of up to 100:1 or even higher. The paraxylene feed, line 6, should be dispersed rapidly upon entering the first reactor. This can be accomplished by using any of the established methods for rapidly dispersing paraxylene-containing feeds in conventional reactors. In a stirred tank reactor 15, as shown in the embodiment of the invention illustrated in FIG. 1, this would include injecting the feed in close proximity to the discharge from an agitator impeller. Although a stirred tank reactor is shown in FIG. 1, other conventional oxidation reactor configurations may also be used with satisfactory results.

The process is carried out in the presence of an oxidation catalyst system, which can be homogeneous or heterogeneous. A homogeneous catalyst is normally used and is selected from one or more heavy metal compounds, such as, for example, cobalt, manganese and/or zirconium compounds. In addition, the catalyst will normally also include an oxidation promoter such as bromine. The catalyst metals and oxidation promoter largely remain in solution throughout the process and are recovered and recycled, following product recovery, with fresh catalyst make-up as a solution.

The feed stream to the first reaction zone, line 10, contains typical oxidation catalyst components (e.g., Co, Mn, Br), but diluted by a factor of about 3 to 5 relative to the catalyst concentration in recycled mother liquor from product recovery, line 11. The catalyst concentration is subsequently raised to more conventional catalyst concentration levels when and as solvent is vaporized and removed overhead in the second reaction zone 20. The total catalyst metals concentration in the first reaction zone will typically lie in the range 150 to 1,000 ppm w/w, whereas the catalyst metals concentration in the second reaction zone will typically lie in the range 500 to 3,000 ppm w/w. When using a Co and Mn metal catalyst system, the total catalyst metals concentration in the first reaction zone should preferably be controlled at greater that about 200 ppm w/w for good catalyst selectivity and activity.

The oxidation reaction is highly exothermic. Depending on the oxygen uptake and solvent ratio and without a means of cooling the reaction, the heat of reaction could raise the temperature of the first reaction medium to a relatively high value, e.g. in excess of 300° C.

Optionally, the first reaction zone may include a cooling coil 18 or employ some other internal or external means for removing heat from the reactor (and reaction medium). It is important that the temperature of the coolant is sufficient to prevent cold spots from forming which can result in localized precipitation of terephthalic acid (TA).

Maintaining the supply of oxygen to the first reaction zone within a predetermined range and controlling the exit temperature, catalyst concentration and residence time of the reaction medium makes it possible to limit the uptake of oxygen within the reaction medium to a value which is less than that required for full conversion of the paraxylene to TA. In a preferred embodiment of the present invention, the oxygen uptake within the reaction medium in the first reaction zone is a value which is less than about 70 percent of the oxygen required for full conversion of the precursor to the corresponding carboxylic acid.

Thus, according to the invention, paraxylene is converted in first reactor 15 primarily to TA intermediates, such as p-tolualdehyde, p-toluic acid and 4-CBA. Under the described process conditions, with effective exit temperature control, the first reactor will not produce any solid TA.

The reaction medium exiting first reactor 15 is fed via line 19 to a second reactor, i.e., oxidation zone, 20, which, as shown, can be a conventional, continuously stirred tank reactor. Simultaneously, the pressure of the reaction medium is reduced to a value in the range of from about 500 kPa to less than 2,500 kPa. As described above, pressure reduction can be conveniently accomplished by passing the reaction medium through one or a plurality of pressure letdown valves or nozzles 21 positioned about the periphery of reactor 20 whereby the reaction medium is dispersed rapidly by injection into an agitator impeller region below the liquid line of the reactor.

Where the source of oxygen to the first reactor includes nitrogen or another sparingly soluble carrier gas, spent or excess air from first reactor 15, line 22, can be mixed with a fresh supply of air or oxygen-containing gas, line 22a, and the resulting mixed feed gas stream introduced and rapidly dispersed into the reaction medium in second reactor 20 by any convenient means. Alternatively, spent or excess air from first reactor 15 can be fed directly to condenser 24, as shown via dotted line 22b, with exclusively fresh air or oxygen-containing gas being fed to second reactor 20.

Where the source of oxygen to the first reactor zone is essentially pure oxygen there will be no spent air from first reactor 15. In this case, exclusively fresh air or oxygen-containing gas is fed to second reactor 20. Where the oxygen supply to first reactor 15 is from an air separation plant, the waste nitrogen from the air separation plant may be mixed with the oxygen-containing gas supply to second reactor 20.

TA will precipitate to form a slurry within reactor 20, and it can be recovered from the reactor system via line 23 using conventional methods. Reactor overhead vapor from reactor 20, which will necessarily contain some acetic acid and water, is condensed via condenser 24, and most of the condensate is returned, i.e., recycled, via line 12 for feed stream make-up to first reactor 15. A proportion of the acetic acid and water condensate stream (so-called water draw off) is diverted to a solvent dehydration system to remove the water of reaction. Optionally, but not shown, a portion of the condensate may be returned to reactor 20, to the reactor headspace, via a reflux slinger, and/or to the reaction zone, via a separate feed line or by mixing with the existing feed stream, line 19. Optionally, but not shown, the overhead vapor from reactor 20 may be fed to a rectifier column, with the bottom product, or condensate, from the rectifier recycled, via line 12, for feed stream make-up to first reactor 15.

FIG. 2 is a simplified schematic diagram of a preferred embodiment of the invention. The first reaction zone, i.e., first reactor 30, according to this embodiment is a plug flow reactor. The term "plug flow reactor" is used herein to define a generally elongated, or tubular, reaction zone in which rapid and thorough radial mixing of the reactants occurs as they flow through the tube or conduit. The invention, however, is intended to embrace any reactor configuration which approximates to a plug flow reaction zone.

As described above in connection with FIG. 1, feed stream 10 is a mixed feed stream comprising (i) recycled solvent, recycled mother liquor and catalyst, via line 11, (ii) second reactor condensate, via line 12, and (iii) fresh acetic acid make-up, via line 13. Optionally, but not shown, control of catalyst concentration in the first reaction zone can be achieved by bypassing some of the catalyst-containing mother liquor, line 11, directly to second reactor 20. The supply of oxygen in this embodiment, line 17a, is essentially pure gaseous oxygen.

The mixed feed stream will generally have a temperature in the range of from 130° C. to 160° C., depending on the temperature of the makeup streams. A temperature in the range of about 140° C. to 160° C. has been found to be suitable for initiating the oxidation reactions.

The pressure of mixed feed 10 is raised to a value in the range of at least, but generally in excess of about, 2,500 kPa by any suitable pumping means 14. The pressure is chosen to ensure that all of the gaseous oxygen, introduced via line 17a, will be readily dissolved in the feed stream ahead of first reactor 30 as shown. The mixed feed stream with dissolved oxygen is then fed simultaneously and continuously into plug flow reactor 30 with paraxylene being fed via line 31, and the reaction is initiated. The paraxylene may optionally be pre-mixed with acetic acid solvent and the mixture fed via line 31. Optionally, but not shown, the paraxylene feed 31 may be pre-mixed with mixed feed stream 10, upstream or downstream of feed pump 14, but upstream of oxygen injector 33. Further optionally, but not shown, a portion of paraxylene feed 31 may bypass reactor 30 and be fed directly to second reactor 20. In cases where a portion of paraxylene feed 31 is fed directly to second reactor 20, the effective solvent: paraxylene mass ratio in the reaction medium in the first reactor will adjust upwardly in response to that portion of the paraxylene feed which bypasses the first reactor, and the resulting mass ratio may reach a value in the range of up to 100:1 or even higher.

Molecular oxygen is dissolved in the mixed feed stream using any convenient in-line mixing device 33 to achieve a concentration of dissolved oxygen in the mixed feed stream of up to 5.0% w/w. Mixing device 33 could be an in-line nozzle arranged to discharge oxygen directly into the feed stream. In-line static mixers (not shown) can also be positioned upstream of first reactor 30 to facilitate mixing.

It is also possible according to the invention to stage the introduction of oxygen, i.e., to introduce the oxygen at a plurality of locations along the length of first reaction zone 30. By staging oxygen injection, the maximum local oxygen concentration is reduced, and this, in turn, permits a reduction in reactor operating pressure.

In practice, feed stream 10 is fed into plug flow reactor 30 with paraxylene to form a reaction medium in which the resulting solvent: paraxylene mass ratio is at least about 5:1, although the solvent: paraxylene mass ratio can be as high as 30:1 or even higher. In a preferred embodiment the solvent: paraxylene mass ratio is in the range of 10–20:1.

Residence time of the reaction medium within plug flow reaction zone 30 is relatively short, i.e., less than 6 minutes.

The reactor 30 shown in FIG. 2 is a shell and tube design. The reaction medium flows through the tubes, while a coolant, e.g., pressurized water (PW), is introduced into the shell side where it boils and is removed as steam (S). A small water purge (boiler blowdown, BB) is taken to control impurity/residue build-up in the water system. The temperature of the reaction medium as it exits first reactor 30 is controlled by controlling the pressure of the produced steam, and hence its temperature.

Controlling the process parameters as described according to the invention makes it possible to limit the uptake of oxygen within the reaction medium in the first reaction zone to a value which is less than that required for full conversion of the paraxylene to TA. Thus, paraxylene is converted in first reactor 30 primarily to TA intermediates, such as p tolualdehyde, p toluic acid and 4 CBA. Under the described process conditions, the first reactor will not produce any solid TA.

Although a shell and tube reactor design is shown in FIG. 2, reactor 30 can be any suitable reactor design with optional heat removal and optional multiple oxygen injection. For example, the reactor can have multiple tube passes, with oxygen injection into the reaction medium upstream of each tube pass. Alternatively, a pumped circulating loop reactor can be employed, with oxygen injection into the loop and heat removal from the loop as illustrated in FIG. 3. Optionally, but not shown, the reactor can comprise an un-cooled (adiabatic) reaction vessel with heat removal from a suitable cooling device downstream of the reaction vessel or in the circulating loop The reaction medium exiting first reactor 30 is fed via line 19 as described above in connection with the process embodiment shown in FIG. 1, to a second reactor, i.e., oxidation zone, 20.

What is claimed is:

1. A process for producing terephthalic acid by catalytic liquid phase oxidation of paraxylene in a solvent selected from an aliphatic carboxylic acid or a non-aliphatic organic acid, said solvent optionally including water, said process comprising:

(a) feeding the solvent, an oxidation catalyst, the paraxylene precursor, and a supply of oxygen to a first reaction zone to form a reaction medium in which the solvent:precursor mass ratio is in the range from 10–20;1 and the operating pressure is at least about 2,500 kPa;

(b) limiting the uptake of oxygen within the reaction medium in said first reaction zone to a value which is less than that required for full conversion of the paraxylene to terephthalic acid such that said terephthalic acid produced in the reaction medium in the first reaction zone remains in solution;

(c) feeding the reaction medium to a second reaction zone while simultaneously reducing the pressure of the reaction medium to a value in the range of from 500 kPa to less than 2,500 kPa;

(d) within the second reaction zone, vaporizing a portion of the solvent present in the reaction medium and removing the vapor from the reactor overhead; and (e) condensing the vapor from the second reaction zone and recycling some or all of the condensate from the second zone to the first reaction zone.

2. The process of claim 1, wherein the uptake of oxygen within the reaction medium in said first reaction zone is limited, to a value less than 70 percent of that required for full conversion of the paraxylene to terephthalic acid.

3. The process of claim 1, wherein less than 10 percent by weight of terephthalic acid precipitates as a solid in the first reaction zone.

4. The process of claim 1, wherein less than 1 percent by weight of the terephthalic acid precipitates as a solid in the first reaction zone.

5. The process of claim 1, wherein there is no precipitation of terephthalic acid as a solid in the first reaction zone.

* * * * *